(12) United States Patent
Singh et al.

(10) Patent No.: US 9,218,460 B2
(45) Date of Patent: Dec. 22, 2015

(54) DEFINING AND MINING A JOINT PHARMACOPHORIC SPACE THROUGH GEOMETRIC FEATURES

(75) Inventors: Ambuj K. Singh, Santa Barbara, CA (US); Sayan Ranu, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 769 days.

(21) Appl. No.: 13/466,669

(22) Filed: May 8, 2012

(65) Prior Publication Data

US 2012/0290624 A1 Nov. 15, 2012

Related U.S. Application Data

(60) Provisional application No. 61/483,907, filed on May 9, 2011.

(51) Int. Cl.
| | |
|---|---|
| G06F 19/00 | (2011.01) |
| G06F 19/10 | (2011.01) |
| G06F 19/28 | (2011.01) |
| G06F 19/16 | (2011.01) |

(52) U.S. Cl.
CPC .............. *G06F 19/705* (2013.01); *G06F 19/16* (2013.01); *G06F 19/28* (2013.01); *G06F 19/707* (2013.01)

(58) Field of Classification Search
None
See application file for complete search history.

(56) References Cited

U.S. PATENT DOCUMENTS

| | | | |
|---|---|---|---|
| 7,188,055 B2 * | 3/2007 | Agrafiotis et al. | 703/2 |
| 2002/0099526 A1 * | 7/2002 | Patterson et al. | 703/1 |
| 2011/0237458 A1 * | 9/2011 | Ofer | 506/9 |

OTHER PUBLICATIONS

Matter et al. (J. Chem. Inf. Comput. Sci. (1999) vol. 39, No. 6:1211-1225).*
Bender et al. (J. Chem. Inf. Comput. Sci. (2004) vol. 44:1708-18).*
Dixon et al. (J. Comput. Aided Mol. Des. (2006) vol. 20:647-71).*
Koutsoukas et al. (Journal of Proteomics (2011) vol. 74:2554-74).*
Wolber et al. (Drug Discovery Today (2008) vol. 13:23-29).*
Yang (Drug Discovery Today (2010) vol. 15:444-450).*
Puigjane et al. (Comb. Chem. And High Throughput Screen. (2008) vol. 11:669-676).*
McGregor et al., "Pharmacophore Fingerprinting. 1. Application to QSAR and Focused Library Design". Journal of Chem. Inf. Comput. Sci., vol. 39, (1999), pp. 569-574.
Saeh et al., "Lead Hopping Using SVM and 3D Pharmacophore Fingerprints". Journal of Chem. Inf. Model., vol. 45, (2005), pp. 1122-1133.

* cited by examiner

*Primary Examiner* — Lori A Clow
(74) *Attorney, Agent, or Firm* — Gates & Cooper LLP

(57) ABSTRACT

A technique for mining pharmacophore patterns including computer-implemented methods for generating a database of pharmacophores and computer-implemented methods for classifying a query molecule with the database of pharmacophores. Generation of the pharmacophore database includes methods of defining a Joint Pharmacophore Space (JPS) using the three-dimensional geometry of pharmacophoric features of all active molecules against multiple targets.

28 Claims, 13 Drawing Sheets

DEFINING AND MINING A JOINT PHARMACOPHORIC SPACE THROUGH GEOMETRIC FEATURES

CROSS-REFERENCE TO RELATED APPLICATIONS

This application claims the benefit of U.S. Provisional Patent Application No. 61/483,907, entitled "DEFINITION AND ANALYSIS OF JOINT PHARMACOPHORIC SPACE THROUGH GEOMETRIC FEATURES," by Ambuj K. Singh and Sayan Ranu, filed May 9, 2011, which application is hereby incorporated by reference herein.

STATEMENT REGARDING FEDERALLY SPONSORED RESEARCH AND DEVELOPMENT

This invention was made with Government support under Grant No. IIS-0917149 awarded by the NSF. The Government has certain rights in this invention.

BACKGROUND OF THE INVENTION

1. Field of the Invention

The invention is generally related to methods for the prediction of the behavior of molecules, including the querying for compounds that have multiple or similar properties, and in particular to pharmacophore analysis and the generation and mining of pharmacophore databases for drug definition and repurposing.

2. Description of the Related Art

Despite steady and significant increases in research and development spending, the number of new drug applications and approvals has been, at best, flat. The low productivity of current target-driven approaches to drug discovery has been ascribed to a number of reasons including limited focus to a single target, and undesirable effects such as toxicity and low efficacy that are discovered too late in the discovery process (see, e.g. Sams-Dodd, F. "Target-based drug discovery: is something wrong?" *Drug Discov. Today* 2005, 10:139-147). As a result, current interest is shifting towards evaluating biological properties at the onset, and attempting to gain a global understanding of the binding activity between compounds and targets (see, e.g. Jenkins, J. L., et al. "In silico target fishing: Predicting biological targets from chemical structure." *Drug Discov. Today: Technol.* 2006, 3: 413-421; Rishton, G. M. "Reactive compounds and in vitro false positives in HTS." *Drug Discov. Today* 1997, 2: 382-384).

There have been a number of attempts to understand the relationship between drug chemical structures and target proteins. In one such study, Yamanishi et al. (see, e.g. Yamanishi, Y., et al. "Prediction of drug-target interaction networks from the integration of chemical and genomic spaces." *Bioinformatics* 2008, 24: 232-240) develop a supervised method to infer unknown drug-target interactions by integrating chemical space and genomic space. The authors make predictions for four classes of important drug-target interactions involving enzymes, ion channels, GPCRs, and nuclear receptors. The method measures chemical similarity in the graph domain by considering the size of the largest common subgraph between two compounds. Keiser et al. (see, e.g. Keiser, M. J., et al. "Relating protein pharmacology by ligand chemistry." *Nat. Biotechnol.* 2007, 25: 197-206) compare protein families based on the chemical structure (Tanimoto coefficient) of the sets of ligands that bind to them. Yildirim et al. (see, e.g. Yildirim, M. A., et al. "Drug-target network." *Nat. Biotechnol.* 2007, 25: 1119-1126) synthesize a global drug-target network consisting of different protein classes with a bipartite graph representation, but the authors do not use the chemical structure information in this analysis.

A number of computational approaches have also been developed to analyze and predict compound-protein interactions. A commonly used method is docking (see, e.g. Cheng, A. C., et al. "Structure-based maximal affinity model predicts small-molecule druggability." *Nat. Biotechnol.* 2007, 25: 71-75; Rarey, M. "A fast flexible docking method using an incremental construction algorithm." *J. Mol. Biol.* 1996, 261: 470-489). However, docking requires 3D structures of proteins, and so cannot be used on a large scale. Wale and Karypis (see, e.g. Wale, N., et al. "Target Fishing for Chemical Compounds Using Target-Ligand Activity Data and Ranking Based Methods." *J. Chem. Inf. Model.* 2009, 49: 2190-2201) develop a technique for "target fishing" (finding all possible targets for a given compound) by analyzing the target-ligand activity matrix using Support Vector Machines (SVM) and perceptrons. Here, each chemical compound is represented by a frequency vector of topological descriptors. Other techniques for such prediction have used nearest-neighbors (see, e.g. Nettles, J. H. "Bridging chemical and biological space: 'target fishing' using 2D and 3D molecular descriptors." *J. Med. Chem.* 2006, 49: 6802-6810), Bayesian models (see, e.g. Nidhi, et al. "Prediction of Biological Targets for Compounds Using Multiple-Category Bayesian Models Trained on Chemogenomics Databases." *J. Chem. Inf. Model.* 2006, 46: 1124-1133), and neural networks (see, e.g. Niwa, T. "Prediction of biological targets using probabilistic neural networks and atom-type descriptors." *J. Med. Chem.* 2004, 47: 2645-2650).

Closer to drug discovery, structure-activity relationships (SAR) have been used to guide the iterative optimization of drug leads. Recently, scientists have focused on improving SAR models by considering additional information besides the known ligands to the target under consideration. These approaches include an iterative SVM where training examples at the decision boundary are added to the training set (see, e.g. Warmuth, M. K., et al. "Active learning with support vector machines in the drug discovery process." *J. Chem. Inf. Comput. Sci.* 2003, 43: 2003), and techniques that refine the SAR score using neighboring protein-ligand pairs in the joint space (see, e.g. Klabunde, T. "Chemogenomic approaches to drug discovery: similar receptors bind similar ligands." *Br. J. Pharmacol.* 2007, 152: 5-7; Jacob, L., et al. "Protein-ligand interaction prediction: an improved chemogenomics approach." *Bioinformatics* 2008, 24: 2149-2156). The latter group of Chemogenomics techniques differ from each other based on the descriptors they use for representing the target, ligand, or the complex or the machine learning method used for prediction (see, e.g. Bock, J. R. "Virtual Screen for Ligands of Orphan G Protein-Coupled Receptors. *J. Chem. Inf. Model.* 2005, 45: 1402-1414; Deng, Z.; et al. "Structural Interaction Fingerprint (SIFt):A Novel Method for Analyzing Three-Dimensional Protein-Ligand Binding Interactions." *J. Med. Chem.* 2004, 47: 337-344; Erhan, D.; et al. "Collaborative Filtering on a Family of Biological Targets." *J. Chem. Inf. Model.* 2006, 46: 626-635: Geppert, H.; et al. "Ligand Prediction from Protein Sequence and Small Molecule Information Using Support Vector Machines and Fingerprint Descriptors." *J. Chem. Inf. Model.* 2009, 49: 767-779; Lapinsh, M.; et al. "Improved approach for proteochemometrics modeling: application to organic compound-amine G protein-coupled receptor interactions." *Bioinformatics* 2005, 21: 4289-4296; Lindstrom, A., et al. "Hierarchical PLS Modeling for Predicting the Binding of a Comprehensive Set of Structurally Diverse Protein-Ligand Complexes." *J. Chem. Inf. Model.* 2006, 46: 1154-1167; Ning, X., et al. "Multi-Assay-Based Structure-Activity Relationship Models: Improving Structure-Activity Relationship Models by Incorporating Activity Information from Related Targets. J. Chem. Inf. Model." 2009, 49: 2444-2456; Strombergsson, H., et al. "Interaction Model Based on Local Protein Substructures Generalizes to the Entire Structural Enzyme-Ligand Space." *J. Chem. Inf. Model.* 2008, 48: 2278-2288; Weill, N., et al. "Development and Validation of a Novel Protein-Ligand Fingerprint To Mine Chemogenomic Space: Application to G Protein-Coupled Receptors and Their Ligands." *J. Chem. Inf. Model.* 2009, 49: 1049-1062). This thread of research again considers global information.

Pharmacophore based screening has also witnessed significant activity in computer aided drug design. A pharmacophore is a spatial arrangement of chemical features that defines a pattern essential for biological activity. Chemical features taken into account in defining pharmacophores usually include hydrogen bond donor/acceptor, charge, hydrophobicity and aromacity. The geometry of the arrangements of pharmacophores is responsible for binding between compounds and targets as well as properties of compounds such as Blood Brain Barrier (BBB) permeability (see, e.g. Zhao, Y. H., et al. "Predicting penetration across the blood-brain barrier from simple descriptors and fragmentation schemes." *J. Chem. Inf. Model.* 2007, 47 : 170-175) and toxicity. A number of excellent tools including Phase (see, e.g. Dixon, S. L., et al. "PHASE: a novel approach to pharmacophore modeling and 3D database searching." *Chem. Biol. Drug Des.* 2006, 67: 370-372; Dixon, S. L., et al. "PHASE: a new engine for pharmacophore perception, 3D QSAR model development, and 3D database screening: 1. Methodology and preliminary results." *J. Comput. Aided Mol. Des.* 2006, 20: 647-671), Catalyst (see, e.g. Kurogi, Y., et al. "Pharmacophore modeling and three-dimensional database searching for drug design using catalyst." *Curr. Med. Chem.* 2001, 8: 1035-1055; Guner, O., et al. "Pharmacophore modeling and three dimensional database searching for drug design using catalyst: recent advances." *Curr. Med. Chem.* 2004, 11: 2991-3005), LigandScout (see, e.g. Wolber, G., et. al. "LigandScout: 3-D pharmacophores derived from protein-bound ligands and their use as virtual screening filters." *J. Chem. Inf. Model.* 2005, 45: 160-169), and MOE (see, e.g. Molecular Operating Environment (MOE), www.chemcomp.com/index.htm) are available for discovering pharmacophores based on a set of actives (and inactives) against a target (usually with an unknown structure), and searching a database for compounds matching the pharmacophore.

However, existing pharmacophore based techniques suffer from two key weaknesses. First, they are able to analyze compounds only on a target-by-target basis, aimed at extracting and optimizing a specific pharmacophore. Such an approach is limited in terms of the search space it can investigate in the drug discovery process. Often, multiple pharmacophoric targets need to be analyzed in search for drugs against diseases such as cancer or AIDS. Second, majority of the pharmacophore based querying and searching techniques assume that some knowledge is available on the geometric properties of the binding pockets in the receptors [Brint, A. T., Willett, P., *J. Mol. Graph.,* 5:49, 1987.], [Alladin.], [Jakes, S. E., and Willett, P., *J. Mol. Graph.,* 4:12, 1986.], [Sheridan, K. P. et al., *J. Chem. Inf. Comp. Sci.,* 29:255, 1989.], [Kuntz, I. D., et al., *J. Md. Bid,* 161: 269, 1982.], [Des Jarlais et al., *J. Med. Chem.,* 29: 2149, 1986.] Based on this knowledge, 3D databases of molecular conformations are scanned to identify potential ligands. Screening of molecular databases is typically done based on some underlying model such as the lock-and-key mechanism. The lock-and-key model assumes that for a molecule to be active its steric characteristics should perfectly complement the shape of the receptor. What is critical to the quality of the prediction is the accuracy of the underlying binding model and the assumptions on the geometries of the binding pockets. Furthermore, if gathering information on the binding pockets is expensive in terms of time or cost, then the utility of the entire searching pipeline is hampered.

The proposed technique answers both of these weaknesses. To drastically increase the search space, the unique concept of the joint pharmacophore space is first defined. The joint pharmacophore space is a database of pharmacophores based on the geometric arrangements of pharmacophoric features of both the actives and inactives against a higher level biological goal. In our technique, this space is directly mined to understand diversity, binding affinities, and biological properties of the actives against a particular disease. Our technique does not assume any knowledge on the geometries of the binding pockets or depend on any underlying binding model. Rather, these geometries are learned from the pharmacophoric space of the training set as long as the set of compounds change in a consistent way while binding to protein targets.

SUMMARY OF THE INVENTION

The present invention discloses a technique for analyzing an entire space of pharmacophores that eliminates the need to optimize pharmacophores against a specific target.

In one aspect of the present disclosure, a computer-implemented method for generating a database of pharmacophores is provided in which the method comprises the steps of defining a joint pharmacophore space comprising a plurality of pharmacophores, each of the plurality of pharmacophores comprising a geometric arrangement of at least three pharmacophoric features, identifying subspaces within the joint pharmacophore space, each subspace having an associated subset of the pharmacophores with similar geometric arrangements, assigning a biological activity property and a representative geometric arrangement for each subspace identified to correlate with a targeted biological activity, and storing the joint pharmacophore space, subspaces, biological activity properties, and representative geometric arrangements.

In one embodiment, a Joint Pharmacophore Space (JPS) of chemical compounds, targets, and physicochemical/biological properties is defined using the 3-dimensional geometry of pharmacophoric features for all active and inactive molecules against multiple targets. The JPS is mined directly to identify pharmacophoric patterns. Identification of similar pharmacophores based on geometric arrangements allows positive/negative properties (such as BBB permeability or hERG receptor activity [see, e.g. Diller, D. J. "In Silico hERG Modeling: Challenges and Progress." *Curr. Comput.-Aided Drug Des.* 2009, 5: 106-121]) to be ascribed to different subspaces. This further allows structure-based filters to be defined early in the drug discovery process.

In another aspect of the present disclosure, methods for mining the JPS are provided. In one embodiment, subspaces that show statistically significant binding activity are identified by clustering pharmacophoric features of compounds in the geometric space and identifying clusters that correlate with a certain biological activity.

In a further aspect of the present disclosure, a computer-implemented method for classifying a query molecule with a database of pharmacophores is provided. The method comprises the steps of obtaining a database of pharmacophores, identifying at least one pharmacophoric feature for a query molecule, defining a three-dimensional coordinate for each pharmacophoric feature of the query molecule, extracting a plurality of geometric arrangements for the query molecule, comparing the plurality of geometric arrangements of the query molecule to the representative geometric arrangements in the database of pharmacophores to classify the query molecule according to its similarity with the representative geometric arrangements, and presenting the classification of the query molecule according to its similarity with the representative geometric arrangements.

In one embodiment, representative pharmacophoric features of the statistically significant subspaces within the JPS are used as geometric keys to convert molecules into feature vectors. As described herein, the descriptor based on significant clusters outperforms Molprint2D, Daylight fingerprints (see, e.g. *Daylight Theory Manual*. Daylight Chemical Information Systems Inc.: Aliso Viejo, Calif., 2008) and 3-point pharmacophore fingerprints (see, e.g. Saeh, J. C., et al. "Lead Hopping Using SVM and 3D Pharmacophore Fingerprints." *J. Chem. Inf. Model*. 2005, 45: 1122-1133) in molecular classification.

The present invention provides a joint space of pharmacophores where the conformations of all known actives and inactives against multiple targets are considered. Such an approach allows the results from a cell-based assay to be deconvoluted into separate activity subspaces, each of which could potentially be responsible for a separate binding. These active subspaces can then be queried to find independent groups of active compounds that can be optimized independently.

The developed system is also able to rank compounds (or compound conformations) based both on proximity to desirable subspaces and distance to undesirable subspaces and then integrate answers across multiple subspaces. Answering proximity or distance queries on a single space can be done by examining the conformations of each compound, extracting the triangles of pharmacophoric points, and measuring the rmsd between the representative cluster center and the compound triangles. The joint space of pharmacophores promises to be a preferred beginning investigation point for medicinal chemists.

BRIEF DESCRIPTION OF THE DRAWINGS

Referring now to the drawings in which like reference numbers represent corresponding parts throughout.

DETAILED DESCRIPTION OF THE INVENTION

In the following description of the preferred embodiment, reference is made to a specific embodiment in which the invention may be practiced. It is to be understood that other embodiments may be utilized and structural changes may be made without departing from the scope of the present invention.

Figure 1:
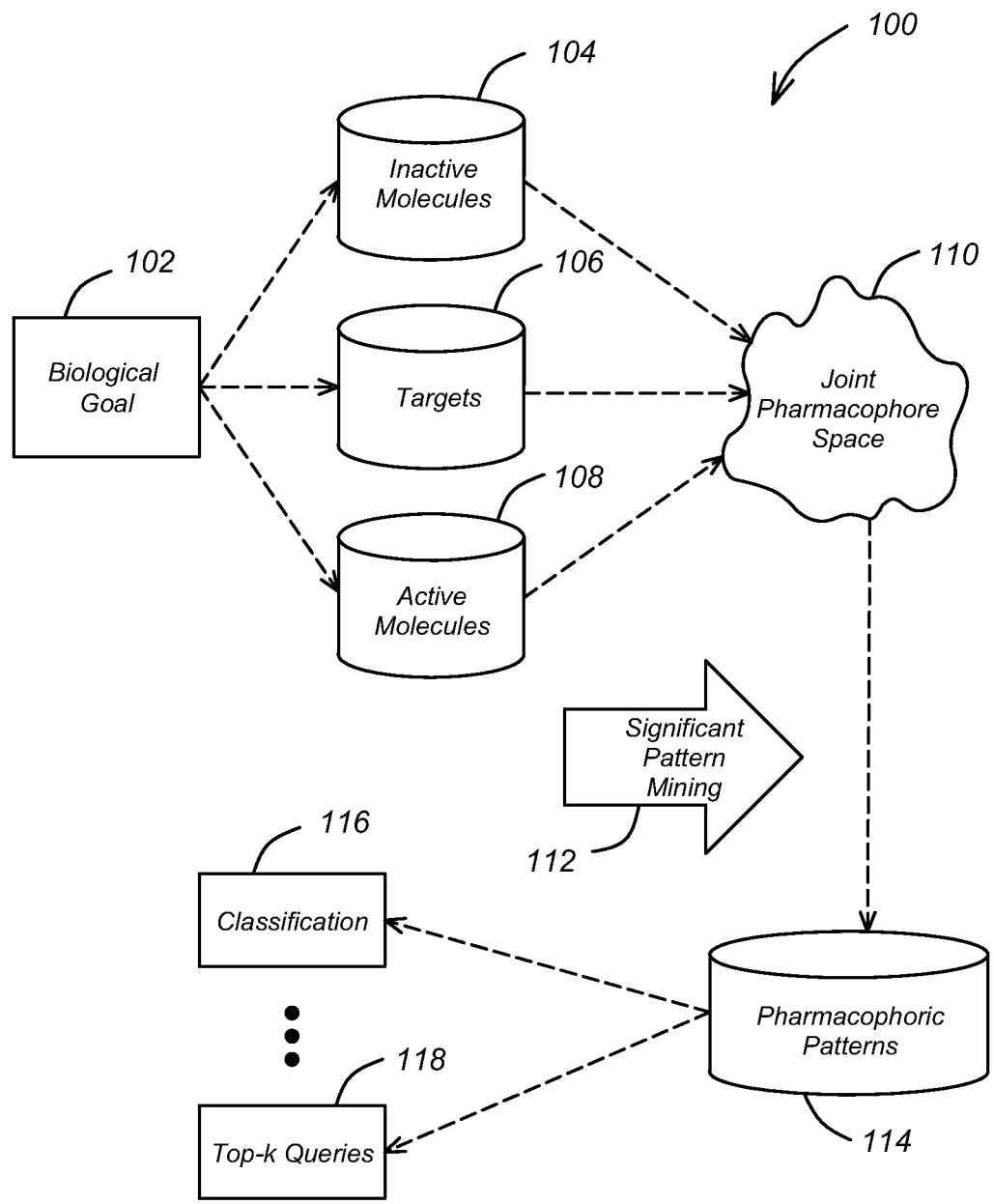
FIG. 1 is a diagram illustrating approach to the generation of a database of pharmacophores.

FIG. 1 is a diagram illustrating an approach 100 to the generation of a database of pharmacophores. A joint pharmacore space 110 is generated from a biological goal 102 which may be manifested in inactive molecules 104, active molecules 108 and targets 106. Pattern matching 112 is used to identify significant pharmacophoric patterns 114, which are used for classification 116 and top-k query 118 purposes.

Figure 2:
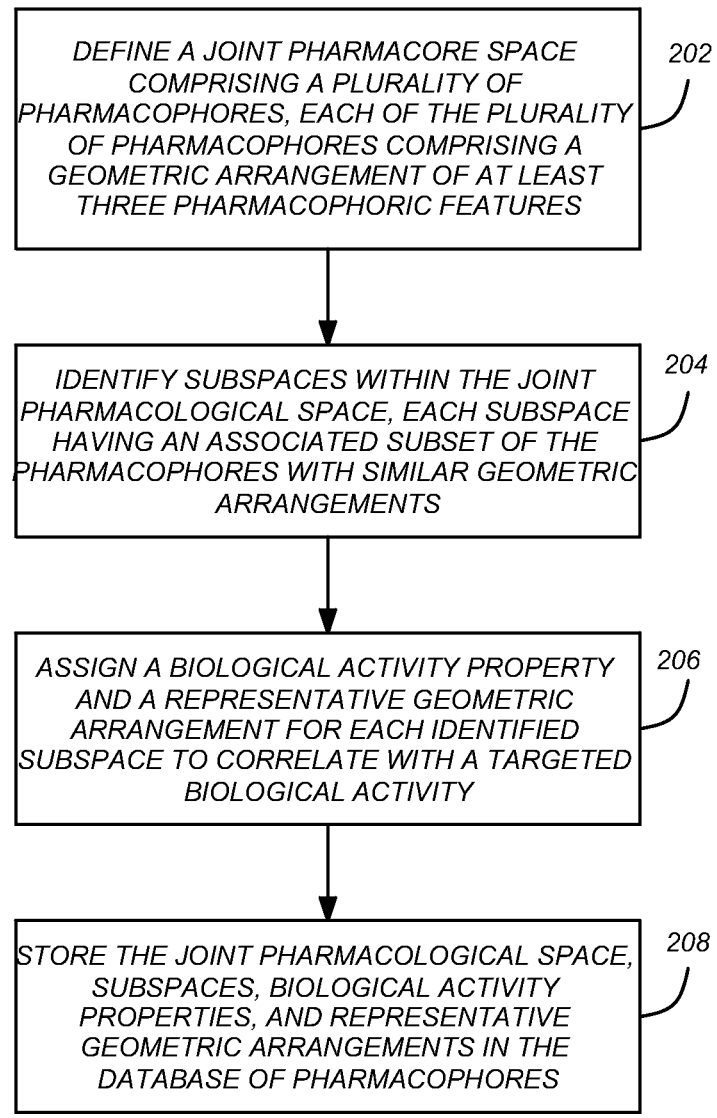
FIG. 2 is a flow chart illustrating exemplary method steps that can be used to generate the database of pharmacophores.

FIG. 2 is a flow chart illustrating exemplary method steps that can be used to generate the database of pharmacophores. In block 202, a joint pharmacological space is identified. The joint pharmacological space comprises a plurality of pharmacophores, each comprising a geometric arrangement of pharmacophoric features.

Figure 3:
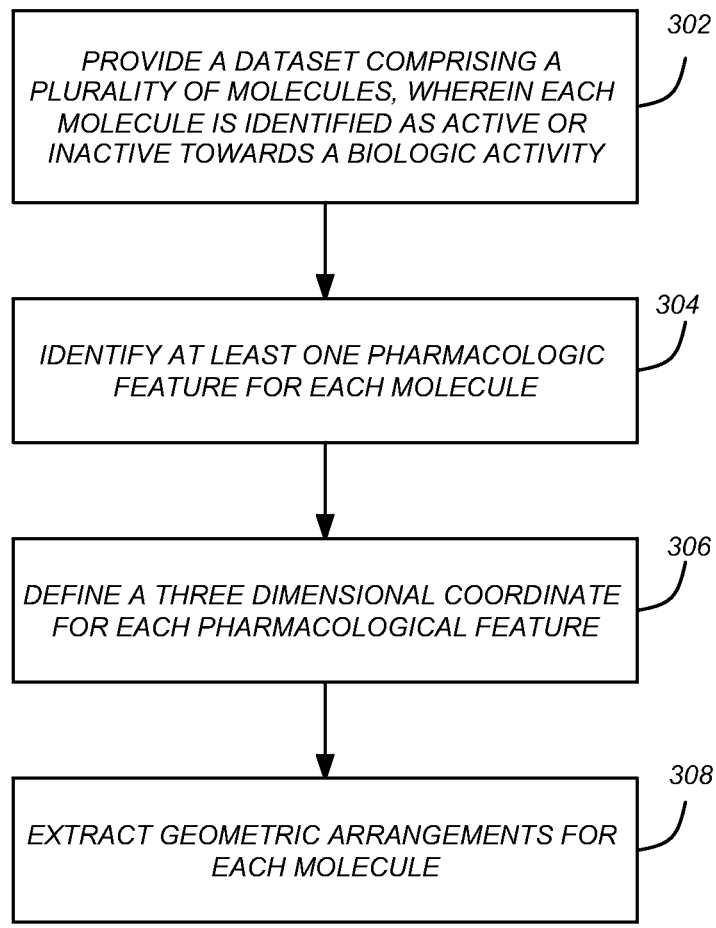
FIG. 3 is a diagram presenting exemplary steps that can be used to define the joint pharmacological space.

FIG. 3 is a diagram presenting exemplary steps that can be used to define the joint pharmacological space. In block 302, a dataset is provided that comprises a plurality of molecules, wherein each molecule is identified as active or inactive towards a biological activity.

Extraction of Pharmacophoric Features

The concept of pharmacophores is based on the kinds of interactions that take place between a set of small molecule ligands and a protein receptor. Typically, low-energy conformations of a molecule are generated and different pharmacophoric features of interest such as hydrogen bond donors and acceptors, aromatic rings, hydrophobic cores, and groups with positive and negative charges are extracted. While each of these features play a role in the binding activity, the exact requirement for a binding to occur typically depends on the presence of multiple such features and the inter-feature geometric distances. At the same time, it is more likely that only a part of the molecule takes active participation in the binding activity rather than the entire structure. As a result, two structurally dissimilar molecules might have affinity towards a similar binding activity, if they share the local structure that is required for the binding. Thus, to model this phenomenon, we need to extract features that are local in nature, but at the same time are able to capture the inter-feature dependencies.

Figure 4:
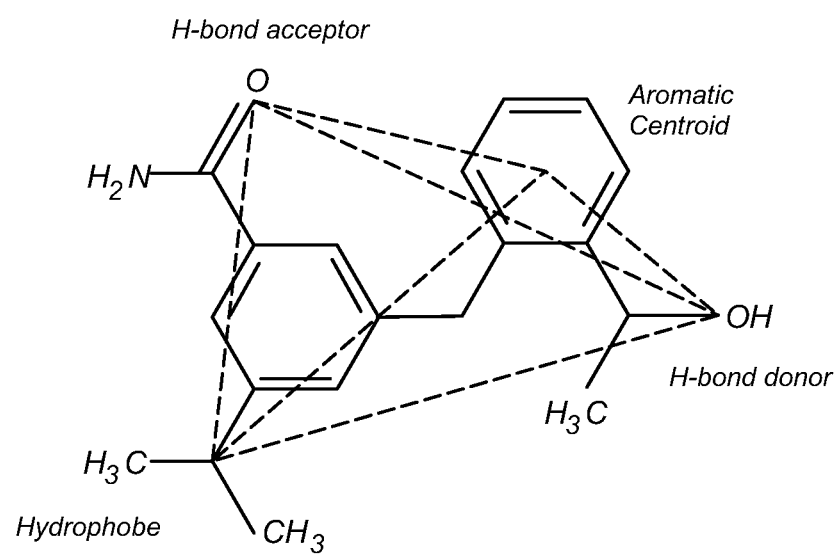
FIG. 4 is a diagram illustrating the extraction of local geometric features of a molecule.

FIG. 4 is a diagram illustrating the extraction of local geometric features of a molecule. Referring back to FIG. 3, one or more and preferably all of the pharmacological features are identified or extracted for each of the plurality of molecules. In block 306, a three dimensional coordinate such is defined for each identified pharmacological feature. In block 308, geometric arrangements defined by the three dimensional coordinates are extracted for each molecule. In one embodiment, the geometric arrangement comprises a triplet. Therefore, triplets may be extracted to characterize the conformation in the geometric space.

The molecule illustrated in FIG. 4 contains four such triplets. In the geometric space, these pharmacophoric triplets take the shape of triangles and can be thought of as the basic building blocks of any local structure that is required for a pharmacophore model. Specifically, even if the local structure for a binding consists of more than three pharmacophoric features, it can be reconstructed by joining the triplets. The advantages of working with triplets are computational efficiency of the ensuing analysis, and minimality, i.e., three pharmacophoric points are usually the minimum number used in pharmacophores. Similar approaches of working with pharmacophoric triplets have been studied before (Saeh, J. C.; Lyne, P. D.; Takas, B. K; Cosgrove, D. A; "Lead Hopping Using SVM and 3D Pharmacophore Fingerprints," *J. Chem. Inf. Model.* 2005, 45, 1122-1133; McGregor, M. J.; Muskal, S. M. Pharmacophore Fingerprinting, 1. Application to QSAR and Focused Library Design, *J. Chem. Inf. Comput. Sci.* 1999, 39, 569-574; Beno, B. R; Mason, J. S., "The design of combinatorial libraries using properties and 3D Pharmacophore Fingerprints," *Drug Discovery Today*, 2001, 6, 251-258. Such triplets have been used to generate "three-point" pharmacophore fingerprints for molecular analysis.

Returning to FIG. 2, block 204 identifies subspaces within the joint pharmacore space wherein each subspace has an associated subset of the pharmacores with similar geometric arrangements.

Figure 5:
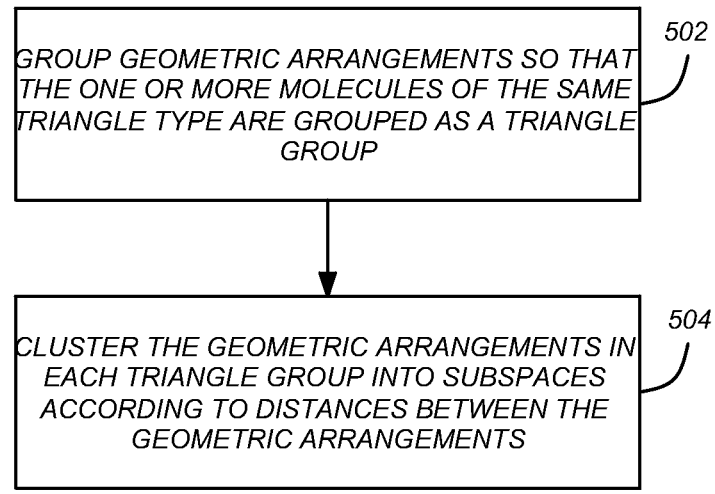
FIG. 5 is a diagram presenting exemplary method steps that can identify subspaces within the joint pharmacophore space that have members with similar geometric arrangements.

FIG. 5 is a diagram presenting exemplary method steps that can identify subspaces within the joint pharmacophore space that have members with similar geometric arrangements. In block 502, the geometric arrangements are grouped so that one or more molecules of the same triangle type are grouped as a triangular group. For example, the extracted triangles can be grouped into set types such that all triangles in a group are mappable to each other, wherein two triangles are mappable to each other if and only if a one-to-one mapping can be established between the vertices of the triangles. The triangle type may be defined by concatenating the types of the pharmacophoric features of its three vertices of the triangle in ascending order. Due to the unique definition of the triangle type, we assure that two triangles are mappable to each other only if they are of the same type.

Figure 6:
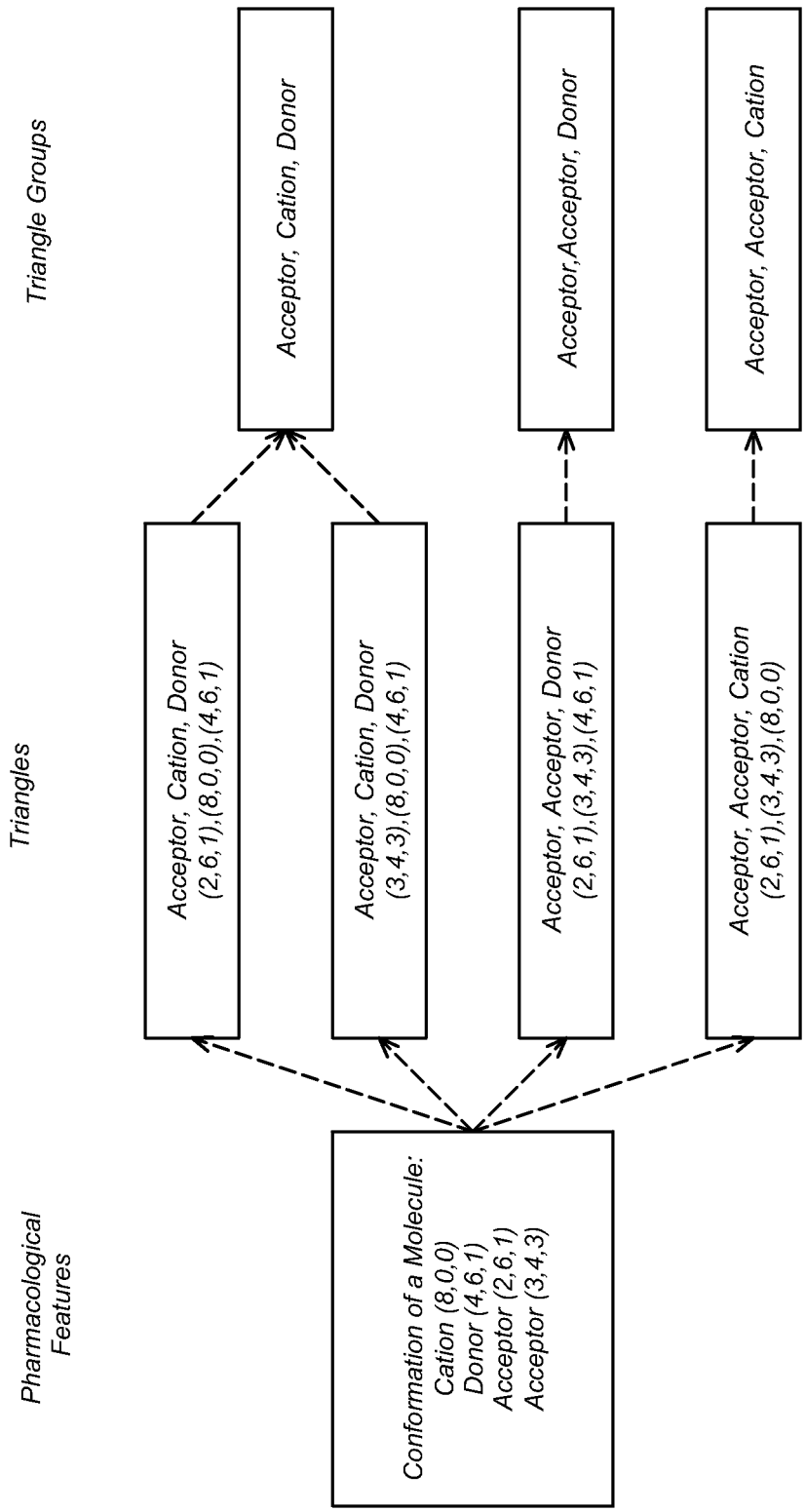
FIG. 6 is an diagram presenting an illustrative example of triangle typing and grouping by type.

FIG. 6 is a diagram presenting an illustrative example of triangle typing and grouping by type. Referring back to the molecule illustrated in FIG. 4, four triangles can be extracted. Each of the four triangles can be associated with two pieces of information: (1) the 3D coordinates of its vertices in the geometric space and the (2) triangle type. In FIG. 6, the molecule has four pharmacophoric features (cation, donor, acceptor, and acceptor) that are defined using the (x,y,z) values. As was true for the molecule shown in FIG. 4, four triangles can be extracted from the molecule. The types of each of these triangles are shown in FIG. 6. The triangles are then grouped into three sets or classes where, the group <Acceptor, Cation, Donor> contains two triangles while the other two groups contain one triangle each. The rationale behind grouping triangles into sets or classes is to keep track of triangles that are comparable to each other. More specifically, a similarity or distance between two triangles can be computed only if they are mappable to each other.

The above feature extraction scheme provides a platform to characterize molecules using local pharmacophoric features in the geometric space. Next, we develop methods to analyze the joint pharmacophore space of molecules to identify interesting subspaces that correlate with a certain binding activity. We assume we have a dataset of molecules that have been assayed against multiple targets but towards a common biological activity. Further, each molecule in the dataset is tagged as either active or inactive.

Figure 7:
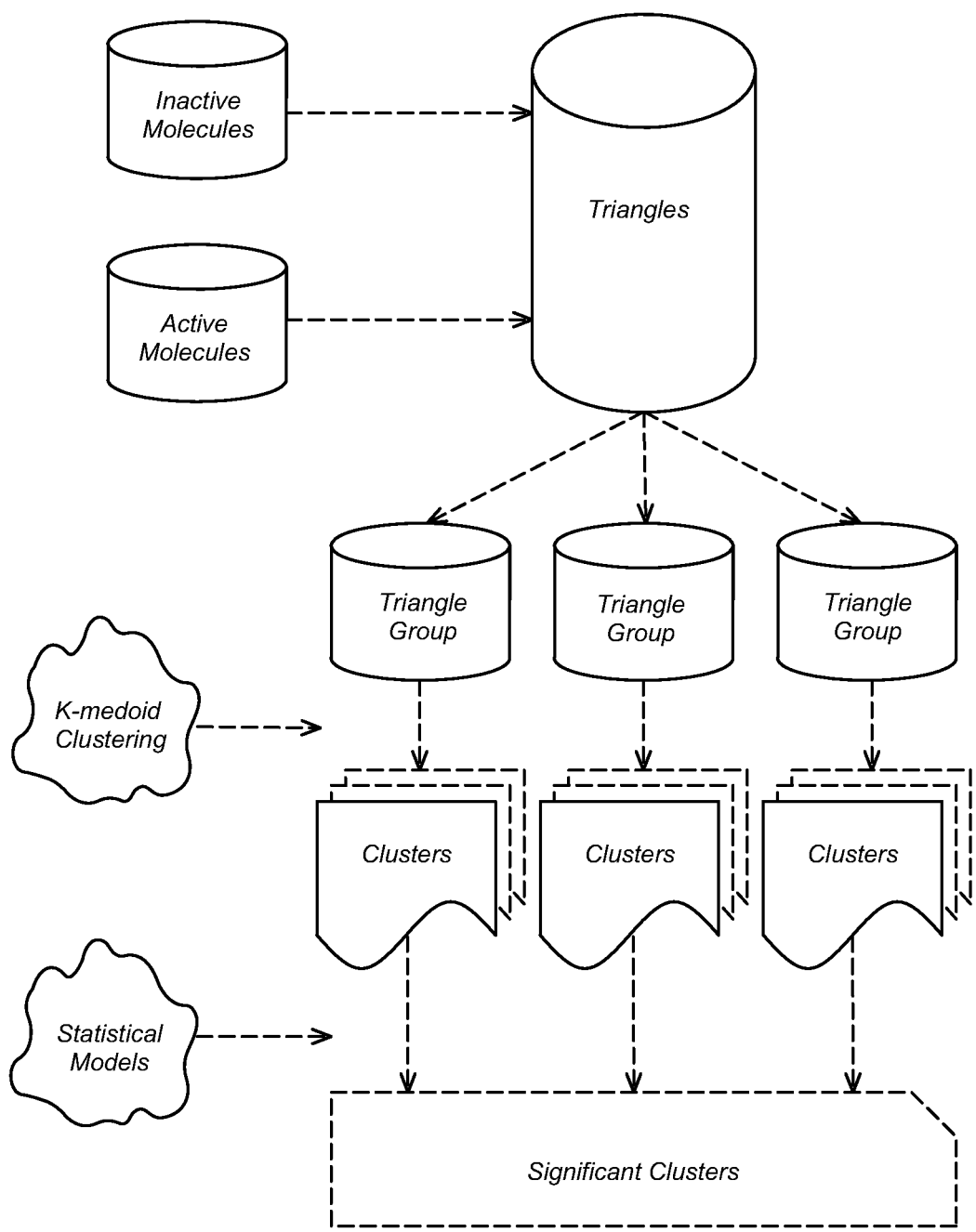
FIG. 7 is a diagram summarizing the process of transforming a dataset of molecules into significant clusters.

FIG. 7 is a diagram summarizing the process of transforming a dataset of molecules into significant clusters. In summary, given a dataset of molecules along with their class labels, pharmacophoric triangles were extracted from conformations of each molecule. As a result, a database of molecules is transformed to a database of triangles. Next, all triangles in the database were grouped into sets based on their types. These groups are clustered, as shown in block 504 of FIG. 5, and significant clusters are later identified from these clusters. The clustering of triangles in each group permits them to be analyzed to identify clusters that are statistically significant, thus allowing the mining geometric structures in the joint pharmacophore space and checking whether a subspace is discriminative towards a specific binding or biological activity. At a high level, different subspaces are annotated with specific chemical/biological properties. In one embodiment, the geometric arrangements in each triangle group are clustered into subspaces according to the distance between the geometric arrangements.

Clustering in the Joint Pharmacophore Space

There are two main components in the clustering process. First, a measure to accurately quantify the similarity or distance between two mappable triangles must be identified. Second, assuming such a distance measure exists, a clustering algorithm that can operate on distance matrices is needed. It is necessary to go to the domain of distance matrices since it is not possible to map triangles to points in the vector space. Although there are hierarchical and graph-based clustering algorithms that can cluster objects based on distance matrices, for our purposes, it is more desirable to use a density-based clustering algorithm (Van Dongen, S. *Ph.D. Thesis*, University of Utrecht, 2000). Thus, techniques for the above two components of the clustering procedure are devised.

To accurately quantify the distance between two triangles, a Kabsch algorithm may be used (Kabsch, W., "A solution of the best rotation to relate two sets of vectors," *Acta Cvystallogr*, 1976, 922). The Kabsch algorithm is a method for calculating the optimal rotation matrix that minimizes the root mean squared deviation (RMSD) between two sets of points. With this algorithm, we compute a distance matrix for each triangle group. Next, to cluster objects using the distance matrix, we use k-medoid clustering. The clustering algorithm proceeds in a manner similar to k-medoid clustering in vector spaces, except for the process of computing the cluster center. In a vector space, the cluster center is computed by simply taking the average of the coordinates of each object in a cluster. However, that is not possible in our case since each object is a triangle.

Figure 8:
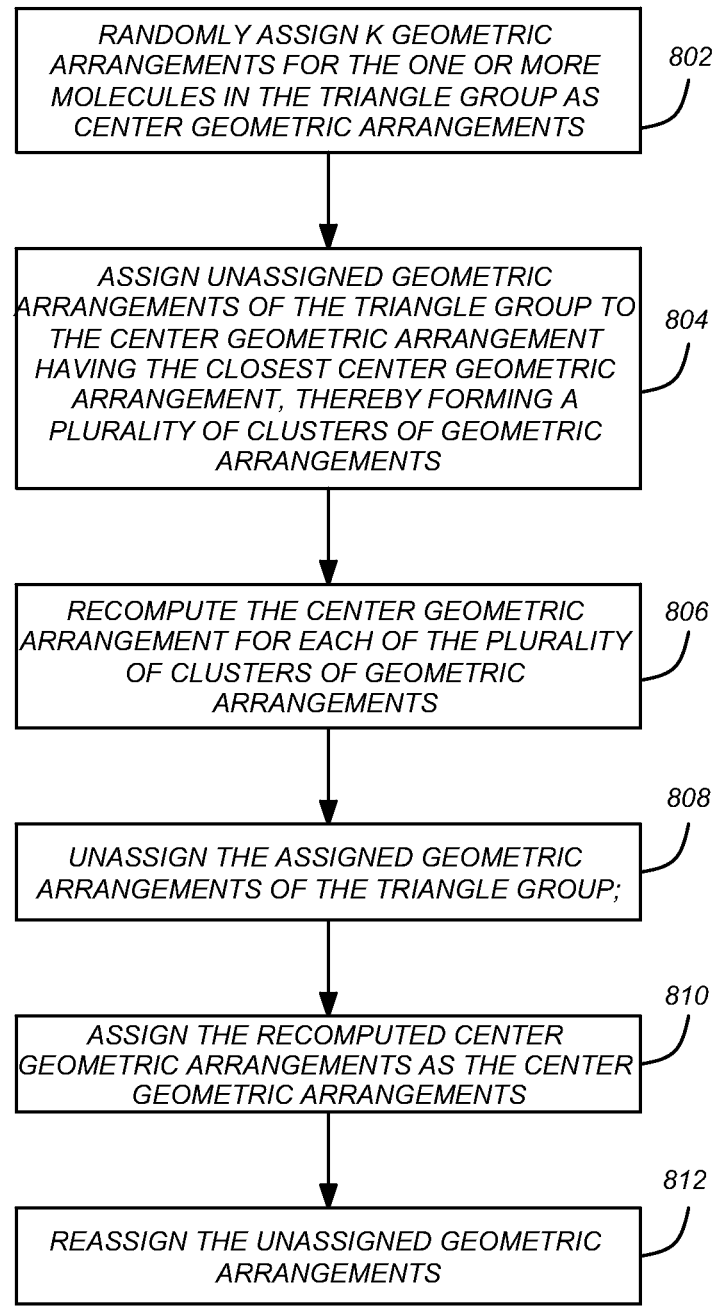
FIG. 8 is a diagram illustrating an algorithm useful for clustering triangles.

FIG. 8 is a diagram illustrating an algorithm useful for clustering triangles. Given the desired number of clusters of triangle, k (which may be user specified), k randomly chosen triangles can be assigned as cluster centers as shown in block 802. Next, all remaining triangles are assigned to the cluster with the closest center, as shown in block 804. Now, the cluster center for each cluster is recomputed, as shown in block 806. This can be performed by choosing the triangle with the minimum average distance to all other triangles in the same cluster. Statistically, the new cluster can be thought of as the median of the cluster. Once the new cluster centers are computed, the remaining triangles are reassigned to appropriate clusters, as shown in blocks 808-812. The process continues in an iterative manner till the cluster centers converge. Finally, the clustered triangles are returned.

Returning to FIG. 2, having identified subspaces or clusters within the joint pharmacological space as shown in block 204, a biological activity property and a representative geometric arrangement for each identified subspace to correlate with a targeted biological activity is assigned, as shown in block 206.

Figure 9:
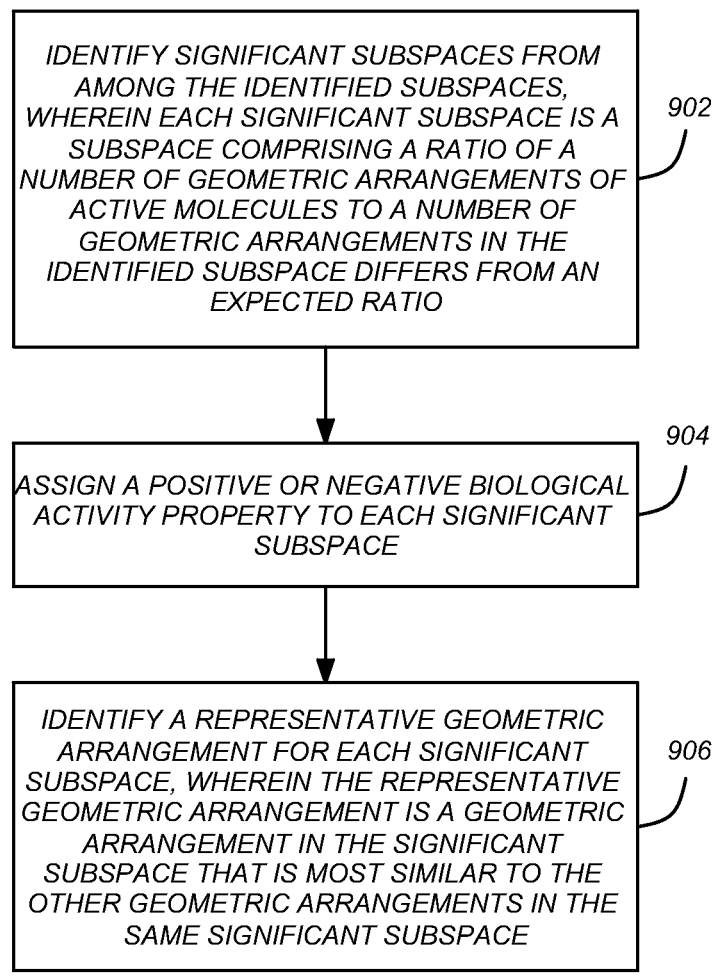
FIG. 9 is a diagram illustrating method steps that may be performed to assign the biological property and representative geometrical arrangement for each identified subspace.

FIG. 9 is a diagram illustrating method steps that may be performed to assign the biological property and representative geometrical arrangement for each identified subspace. In block 902, significant subspaces or clusters are identified from among the identified subspaces or clusters, wherein significant subspaces are determined as those having a ratio of a number of geometric arrangements of active molecules to a number of geometric arrangements in the identified subspace that differ from an expected ratio.

Identifying Significant Clusters

Once the joint pharmacophore space is clustered, the clustered subspaces are analyzed and evaluated for biologically/chemically useful properties. More specifically, if the distribution of triangles from conformations of active molecules in a cluster deviates significantly from the expected ratio, then the cluster is discriminative in nature. Thus, to identify such clusters, we develop methods to analyze the statistical significance of a cluster. Statistically significant clusters can then be applied for higher level mining tasks such as molecular classification and top-k similarity queries.

First, we formalize the idea of positive and negative clusters. Given a dataset D of molecules, let A be the set of active molecules in D. Further, given a cluster of triangles C originating from conformations of molecules in D, let P be the set of triangles from conformations of active molecules in C. The expected ratio r is defined as the expected ratio of triangles originating from conformations of active molecules in any given cluster C. Mathematically, the expected ratio r is $$r = \frac{|A|}{|D|} \quad (1)$$

Further, define a cluster as a positive cluster if the ratio of triangles from conformations of active molecules (active triangle) is significantly more than the expected ratio. Mathematically, cluster C is positive if it satisfies the following condition:

$$C \text{ is positive: } \frac{|P|}{|C|} \geq \delta r \quad (2)$$

where $\delta$ is a user-defined threshold parameter.

And define a cluster as a negative cluster if the ratio of triangles from active class is significantly less than the expected ratio, as mathematically defined below $$C \text{ is negative: } \frac{|P|}{|C|} \leq \delta r \quad (3)$$

If a cluster is positive or negative, then it is a subspace of interest. Since the distribution of active triangles in such a subspace deviates from the expected behavior, they have more discriminative power. Positive and negative clusters can be employed to better understand the binding behavior of molecules and applied in higher level querying and mining tasks. For example, the triangle representing the cluster center can be employed to search molecules that display a desired activity. We show one such application in molecular classification in the next section.

Besides the identification of positive and negative clusters, an extensive significance analysis can also be performed using the idea of p-value. The p-value of a cluster C that contains the set of active triangles P is defined as the probability that a random cluster of triangles contains more than |P| active triangles.

Figure 10:
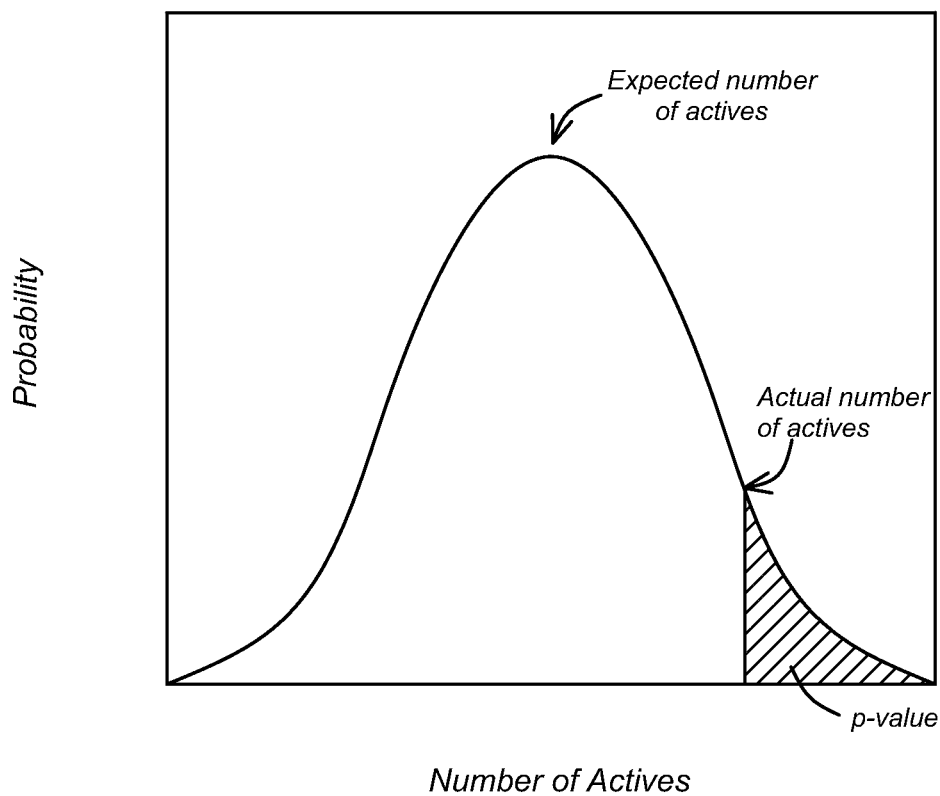
FIG. 10 is a diagram showing how the p-value may be determined from a probability density function.

FIG. 10 is a diagram showing how the p-value may be determined from a probability density function. As shown, the p-value of a cluster can be calculated by measuring the area to the right of the actual number of actives under its probability distribution function (pdf). Clearly, lower the p-value of a cluster, the more significant it is. The distribution of active triangles in a cluster can be modeled as a binomial. Each triangle in a cluster can be viewed as a trial, and a triangle being active can be regarded as "success". A cluster containing m triangles will involve m trials. The number of active triangles in the cluster is the number of successes. Therefore, the probability of a cluster C having $\mu$ active triangles is:

$$P(C; \mu) = \binom{m}{\mu} r^\mu (1-r)^{m-\mu} \quad (4)$$

where r is the expected ratio computed using Equation 1, and m=|C|.

The pdf of C can be generated from Equation (4) by varying $\mu$ in the range [0,m]. Therefore, given the actual number of active triangles $\mu_0$=|P| in C, its p-value can be calculated by measuring the area under the pdf in the range [$\mu_0$,m], which is $$p\text{-}value(C, \mu_0) = \sum_{i=\mu_0}^{m} P(C; i) \quad (5)$$

Equation 5 reduces to the regularized Beta function I(P(C); $\mu_0$,m), which is faster to compute. Wolfram, MathWorld, http://mathworld.wolfram.com/BinomialDistribution.html (accessed Nov. 16, 2010). The p-value of a negative cluster can be computed using the same framework, except for the change of using an expected ratio of inactives rather than expected ratio of actives.

Returning to FIG. 9, a positive or negative biological activity property is assigned to each significant subspace, as shown in block 904. Finally, a representative geometric arrangement for each significant subspace is identified, wherein the representative geometric arrangement is a geometric arrangement in the significant subspace that is most similar to the other geometric arrangements in the same significant subspace, as shown in block 906. This can be accomplished via the kernel function described below.

Molecular Classification

In this section, we demonstrate the application of mining the joint pharmacophore space in molecular classification. Pharmacophores corresponding to significant cluster centers are indicative of the selective chemical and biological activity. This can be used for in silico prediction of activity of new molecules through a classification approach.

Figure 11:
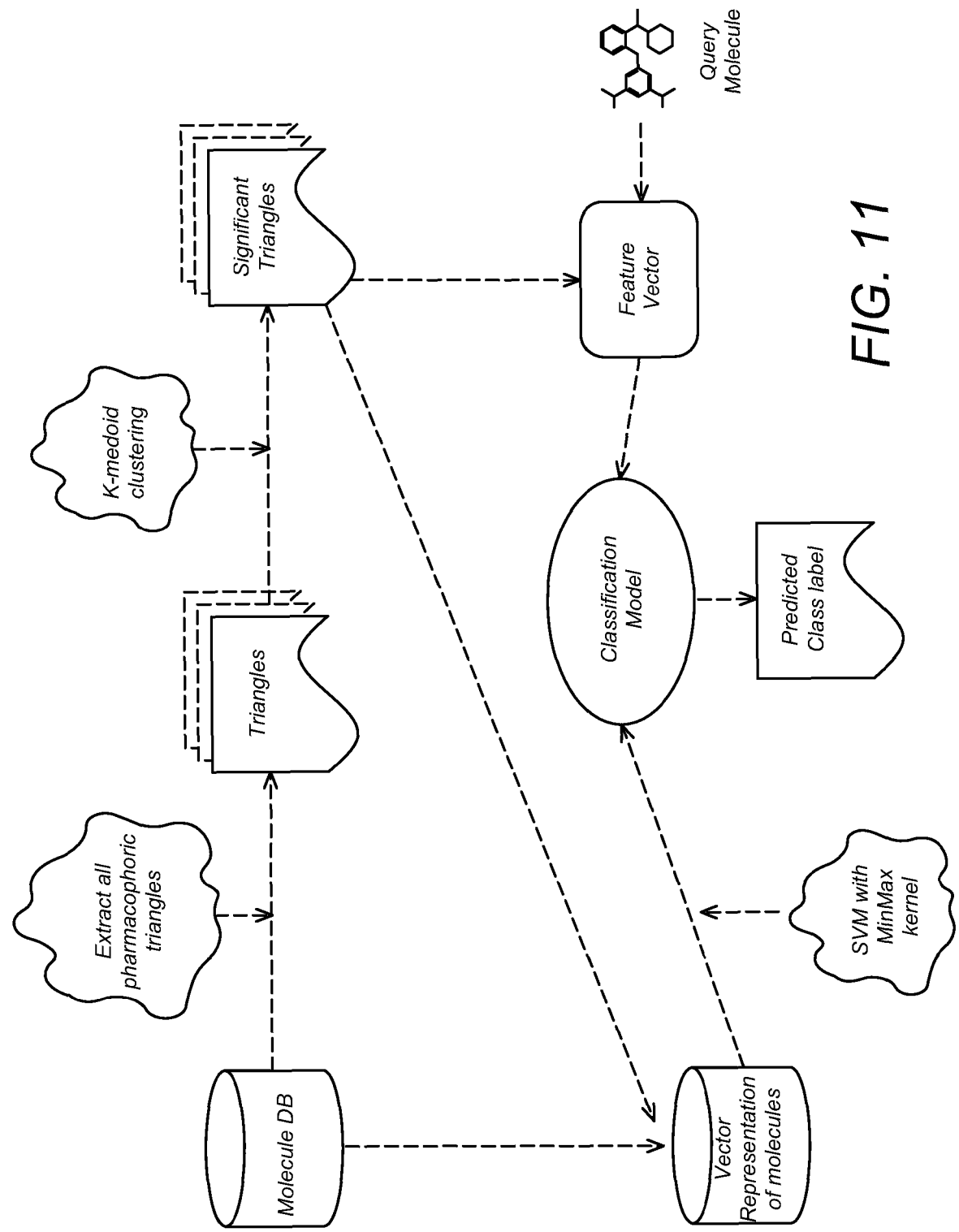
FIGS. 11 and 12 are diagrams outlining of the a method to classify molecules based on significant subspaces mined from the joint pharmacophore space.
Figure 12:
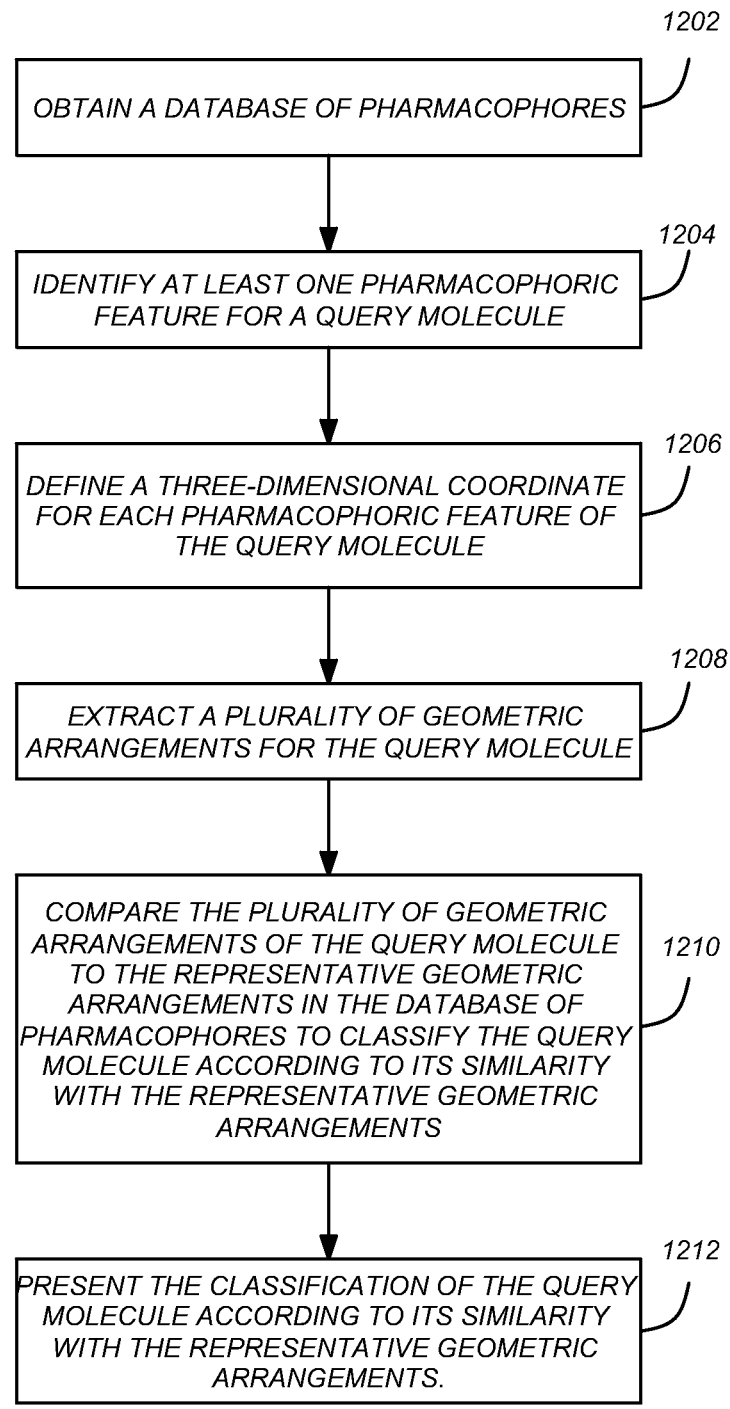

FIGS. 11 and 12 are diagrams outlining a method to classify molecules based on significant subspaces mined from the joint pharmacophore space. Given a training dataset with molecules labeled as active or inactive, we first cluster the joint pharmacophore space as described in the previous section. Next, we identify all significant triangles in this joint pharmacophore space (e.g. using k-medoid clustering) and use them as pharmacophoric keys. A triangle is a significant triangle if it forms the cluster center of a positive or negative cluster.

The rationale behind using significant triangles as pharmacophoric keys is to characterize molecules based on how closely they align to the discriminative subspaces within the joint pharmacophore space defined above. Since each of the positive or negative clusters deviates from the expected behavior, their centers have a high discriminative power and provide an excellent platform to build classifiers.

Once the significant triangles are identified, all query molecules in the training dataset are converted to a feature vector where each dimension corresponds to a specific significant triangle. Converting a molecule to a feature vector may be accomplished as follows. Given a query molecule m, first, all triangles in m are identified. Next, each of the extracted triangles is compared to the significant triangles to identify the closest significant triangle. If the root mean square distance of the closest significant triangle is within a user-specified threshold, then the dimension corresponding to the significant triangle is incremented. Essentially, for each triangle in the query molecule, we check whether it aligns well with any of the significant triangles.

Based on this result, the information is stored in the vector representation of the molecule. Ultimately, the vector representation of the query molecule is returned. Given the vector representation of the molecule in the training dataset, we use support vector machines (SVM) to develop the training model (Vaptuk, V., "Statistical Learning Theory," John Wiley, New York, N.Y., USA). One key issue that affects the performance of SVM is the choice of kernel. The kernel function computes the similarity between two input vectors. Theoretically, any kernel can be used as long as the similarity matrix computed by the kernel function satisfies the Mercer's conditions (Swamidass, S. J.; Chen, J.; Bruand, J.; Phung, P.; Ralaivola, L.;

Baldi, P., "Kernels for small molecules and the prediction of mutagenicity, toxicity and anti-cancer activity," *Bioinformatics* 2005, 21, 359-368.). We use the MinMax kernel to build the classification model. The MinMax kernel function for vectors $X=[x_1, \ldots, x_n]$ and $Y=[y_1, \ldots, y_n]$ is defined as follows:

$$K(X, Y) = \frac{\sum_i \min(x_i, y_i)}{\sum_i \max(x_i, y_i)} \forall i \quad (6)$$

The MinMax kernel function is similar to the Tanimoto coefficient, which has been extensively used in the chemoinformatics community (see Bajorath, J., "Integration of virtual and high-throughput screening," *Nat. Rev. Drug. Discovery*, 2002, 1, 882-894; Bohm, H.-J., Schneider, G., "Virtual Screening for Bioactive Molecules," John Wiley & Sons, Inc.: New York, N.Y., USA, 2000; Whittle, M., Gillet, V. J., Willett, P., Alex, A, Loesel, J., "Enhancing the effectiveness of virtual screening by fusing nearest neighbor lists: a comparison of similarity coefficients," *J. Chem. Inf. Comput. Sci.*, 2004, 44, 1840-1848). For binary vectors, both kernels return the same similarity value. However, since our vectors contain actual counts, we use the MinMax kernel. The MinMax kernel has been shown to satisfy the Mercer's conditions. Once the classification model is built, a query molecule (specifically, its 3D conformation) is converted to a feature vector using the same procedure in the algorithm recited above. Next, the vector is provided as input to the classifier to obtain its predicted class.

FIG. 12 is a diagram presenting illustrative method steps that can be used to classify a query molecule with a database of pharmacophores. In block 1202, database of pharmacophores is obtained. In block 1204, at least one pharmacophoric measure is identified for a query molecule. In block 1206, a three-dimensional coordinate for each phramacophoric feature of the query molecule is defined. In block 1208, a plurality of geometric arrangements is extracted for the query molecule. In block 1210, a plurality of geometric arrangements of the query molecule is compared to the representative geometric arrangements in the database of pharmacophores to classify the query molecule according to its similarity with the representative geometric arrangements. Finally, in block 1212, the classification of the query molecule is presented according to its similarity with the representative geometric arrangements.

Drug Repurposing

Mining the JPS 110 also finds application in drug repurposing. Currently, the process of drug discovery comprises of seven different steps: disease selection, target hypothesis, lead compound identification, lead optimization, pre-clinical trial, and finally clinical trial. Unfortunately, more than 90% of the molecules selected in the lead identification step are discarded in lead optimization due to "non-drug-like" properties such as toxicity and harmful side-effects. This high discard rate of the traditional drug discovery pipeline acts as the single most influential barrier to making drug discovery more cost efficient.

To counter the limitation of the traditional drug discovery pipeline, an attractive proposition is drug repurposing: finding new uses for existing drugs. A drug can be 'repurposed' if it binds to a secondary target that is also known to cure a certain disease; in other words, a drug that can cure multiple diseases. Drug repurposing allows us to bypass the entire lead optimization step and thereby lowering the risk and cost of drug discovery and development.

In drug repurposing, the core problem is to identify molecules whose structures are compatible to multiple desired targets. Mining the JPS 100 provides an efficient route towards such discoveries by studying the structures of known drugs and analyzing if they contain the geometries required to bind to multiple protein targets. More specifically, first, a training set can be constructed containing all known drugs (corresponding to multiple diseases). Such a training data set can be constructed from the various public repositories such as PubChem [pubchem.ncbi.nlm.nih.gov]and ChEMBL [www.ebi.ac.uk/chembldb]. Next, all triangles can be extracted from the training data set to create the JPS 100. The JPS 100 can next be clustered to define the various activity subspaces. For the problem of drug-repurposing, a cluster is statistically significant if it is over-populated with triangles from drugs corresponding to a single disease. Such a subspace indicates the geometry required for a molecule to be active against the corresponding disease. Based on this analysis, statistically significant clusters can first be extracted and then tagged with the disease that it corresponds to. From this tagged list, an activity profile can be generated for each disease that contains all the required geometries for a molecule to be active. The activity profile can then be leveraged to identify drugs that can be repurposed. More specifically, if a drug satisfies the activity profiles of multiple diseases then it is predicted as a candidate that can be repurposed.

Hardware and Software Environment

Figure 13:
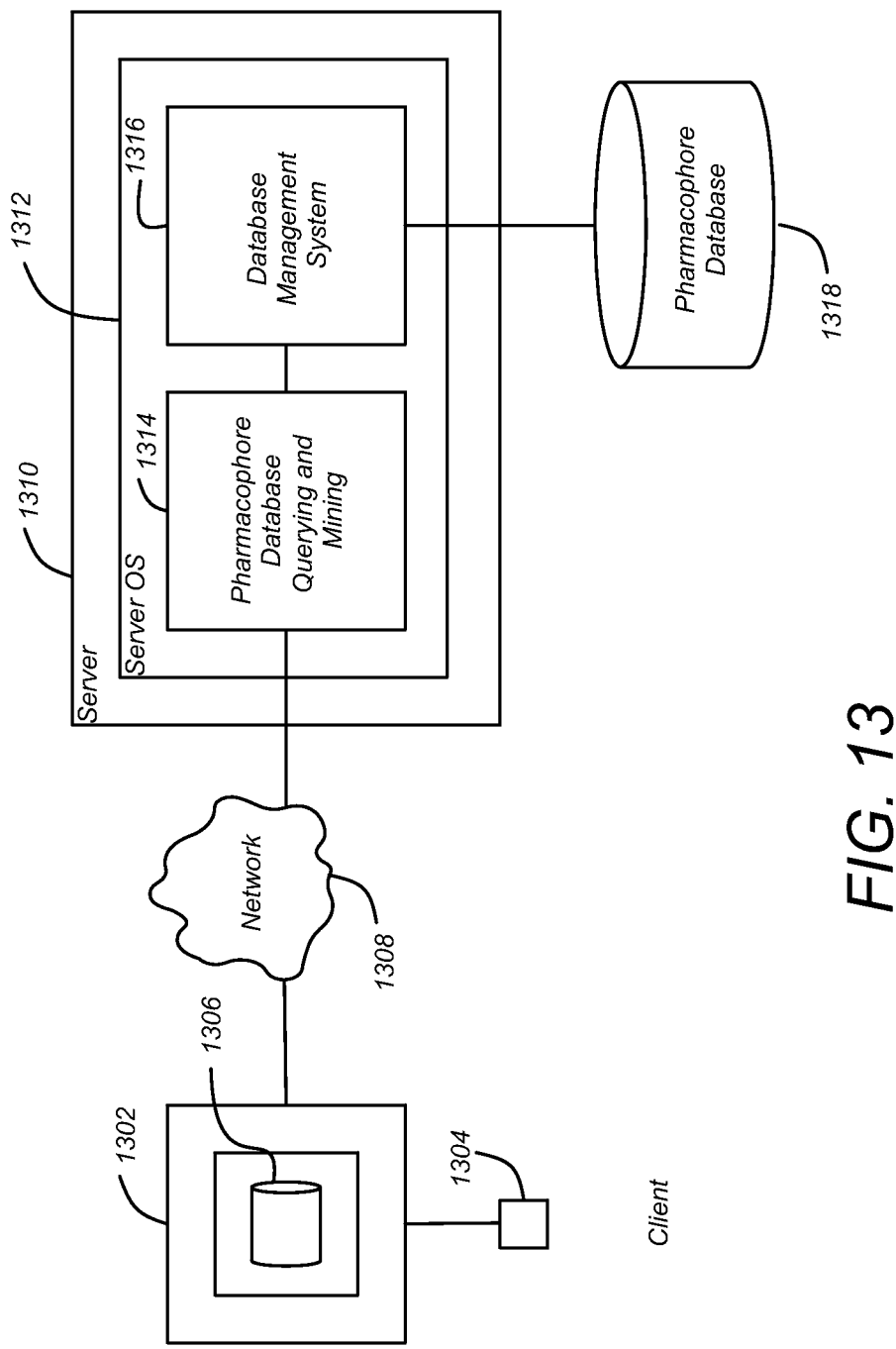
FIG. 13 schematically illustrates a hardware and software environment that can be used to practice embodiments of the invention.

FIG. 13 schematically illustrates a hardware and software environment in accordance with one or more embodiments of the invention, and more particularly, illustrates a typical distributed computer system 1300 using a network 1308 to connect one or more client computers 1302 to one or more server computers 1310. A typical combination of resources may include a network 1308 comprising the Internet, LANs, WANs, or the like, clients 1302 that are personal computers or workstations, and servers 1310 that are personal computers, workstations, minicomputers, or mainframes. Additionally, both client 1302 and server 1310 may receive input (e.g., cursor location input) and display a cursor in response to an input device such as cursor control device 1304.

In one or more embodiments of the invention, the client 1302 may execute a pharmacophore database application 1306, which performs some or all of the logic described herein, and which communicates with one or more server computers 1310. The server computers 1310, in turn, each execute under the control of a server operating system (OS) 1312. In addition, the server computers 1310 may execute a pharmacophore database querying and mining application 1314, which performs some or all of the logic described herein. The pharmacophore database querying and mining application 1314 may access and/or manipulate data stored in a pharmacophore database 1318 by means of a database management system (DBMS) 1316.

Generally, these components 1306, 1312, 1314, 1316 and 1318 comprise instructions and/or data that is embodied in or retrievable from device, medium, signal, or carrier, e.g., a data storage device, a data communications device, a remote computer or device coupled to the computer 1302, 1310 via a network or via another data communications device, etc. Moreover, this logic and/or data, when read, executed, and/or interpreted, results in the steps necessary to implement and/or use the present invention being performed.

Thus, embodiments of the invention may be implemented as a method, apparatus, or article of manufacture using standard programming and/or engineering techniques to produce software, firmware, hardware, or any combination thereof. The term "article of manufacture" (or alternatively, "computer program product") as used herein is intended to encompass logic and/or data accessible from any computer-readable device, carrier, or media.

Those skilled in the art will recognize many modifications may be made to this exemplary environment without departing from the scope of the present invention. For example, those skilled in the art will recognize that any combination of the above components, or any number of different components, including different logic, data, different peripherals, and different devices, may be used to implement the present invention, so long as similar functions are performed thereby.

Conclusion

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

All publications, patents, and patent applications cited herein are hereby incorporated by reference herein.

What is claimed is:

1. A computer-implemented method for generating a database of pharmacophores for use in classifying one or more query molecules for drug discovery and repurposing, comprising the steps of:
   (a) defining, in one or more computers, a joint pharmacophore space comprising a plurality of pharmacophores, each of the plurality of pharmacophores comprising a geometric arrangement of at least three pharmacophoric features, and the defining step comprising the steps of:
      (i) providing a dataset comprising a plurality of molecules, wherein each of the molecules is identified as active or inactive towards a biological activity;
      (ii) identifying the pharmacophoric features for each of the molecules;
      (iii) defining three-dimensional coordinates for the pharmacophoric features; and
      (iv) extracting the geometric arrangement from a triplet of the three-dimensional coordinates, wherein the triplet defines a triangle type and the triangle type is determined from an order of the pharmacophoric features;
   (b) converting, in one or more computers, molecules into feature vectors by identifying subspaces within the joint pharmacophore space, each subspace having an associated subset of the pharmacophores with similar geometric arrangements, and the identifying step comprising the steps of:
      (i) grouping the geometric arrangements according to the triangle type, wherein the geometric arrangements with similar triangle types are grouped as a triangle group; and
      (ii) clustering the geometric arrangements in each triangle group into the subspaces according to distances between the geometric arrangements;
   (c) assigning, in one or more computers, a biological activity property and a representative geometric arrangement for each subspace identified to correlate with a targeted biological activity; and
   (d) storing, in one or more computers, the joint pharmacophore space, subspaces, biological activity properties, and representative geometric arrangements in the database of pharmacophores.

2. The computer-implemented method of claim 1, wherein each triplet defines a triangle having vertices corresponding to the three-dimensional coordinates.

3. The computer-implemented method of claim 1, wherein the order is user-defined.

4. The computer implemented method of claim 1, wherein the geometric arrangements in each triangle group that satisfy a user-defined similarity criteria are clustered as a subspace.

5. The computer-implemented method of claim 1, wherein the step (ii) of clustering the geometric arrangements in each triangle group comprises the steps of:
   computing one or more center geometric arrangements in the triangle group;
   assigning the geometric arrangements in the triangle group to a closest one of the center geometric arrangements, thereby forming clusters of the geometric arrangements.

6. The computer-implemented method of claim 5, wherein the center geometric arrangements in the triangle group are computed from the geometric arrangement having a minimum average distance to other geometric arrangements in the clusters of geometric arrangements.

7. The computer-implemented method of claim 1, wherein step (c) of assigning a biological activity property comprises the steps of:
(i) mining significant subspaces from among the identified subspaces, wherein the significant subspaces have a ratio of a number of geometric arrangements of active molecules to a total number of geometric arrangements that differs from an expected ratio;
(ii) assigning a positive or negative biological activity property to each significant subspace;
(iii) identifying a representative geometric arrangement for each significant subspace, wherein the representative geometric arrangement is most similar to other geometric arrangements in each significant subspace.

8. The computer-implemented method of claim 7, wherein the subspaces are identified as significant subspaces if the ratio of the number of geometric arrangements of active molecules to the total number of geometric arrangements differs from the expected ratio in an amount greater than or equal to a user-defined threshold.

9. The computer-implemented method of claim 8, wherein a positive biological activity property is assigned to a significant subspace having a ratio of the number of geometric arrangements of active molecules to the total number of geometric arrangements that is greater than the expected ratio and a negative biological activity property is assigned to a significant subspace having a ratio of the number of geometric arrangements of active molecules to the total number of geometric arrangements that is less than the expected ratio.

10. The method of claim 1, wherein:
the dataset is a dataset of known drugs;
the step (c) of assigning the biological activity property and a representative geometric arrangement for each subspace identified to correlate with a targeted biological activity comprises the steps of:
mining significant drug subspaces from among the identified subspaces, wherein the significant drug subspaces have a number of geometric arrangements associated with a drug corresponding to a single disease greater than an expected number of geometric arrangements; and
tagging each of the mined significant drug subspaces with the corresponding disease.

11. The method of claim 10, further comprising the steps of:
generating an activity profile for each disease associated with the drug; and
identifying a repurposed drug from the activity profile for more than one disease.

12. The computer-implemented method of claim 1, wherein the triangle includes vertices corresponding to the three-dimensional coordinates of the triplet and the triangle type.

13. The computer-implemented method of claim 12, wherein the triangle type is established by a user-defined order of the pharmacophoric features of the three-dimensional coordinates in the triplet.

14. A computer-implemented method of classifying a query molecule with a database of pharmacophores, comprising:
(a) obtaining, in one or more computers, a database of the pharmacophores as generated in claim 1;
(b) identifying, in one or more computers, at least one pharmacophoric feature for a query molecule;
(c) defining, in one or more computers, a three-dimensional coordinate for each pharmacophoric feature of the query molecule;
(d) extracting, in one or more computers, a plurality of geometric arrangements for the query molecule;
(e) comparing, in one or more computers, the plurality of geometric arrangements of the query molecule to the representative geometric arrangements in the database of pharmacophores to classify the query molecule according to its similarity with the representative geometric arrangements; and
(f) presenting, in one or more computers, the classification of the query molecule according to its similarity with the representative geometric arrangements.

15. A computer-implemented apparatus for generating a database of pharmacophores for use in classifying one or more query molecules for drug discovery and repurposing, comprising:
one or more computers; and
one or more processes performed by the one or more computers, the processes configured to perform the steps of:
(a) defining a joint pharmacophore space comprising a plurality of pharmacophores, each of the plurality of pharmacophores comprising a geometric arrangement of at least three pharmacophoric features, and the defining step comprising the steps of:
(i) providing a dataset comprising a plurality of molecules, wherein each of the molecules is identified as active or inactive towards a biological activity;
(ii) identifying the pharmacophoric features for each of the molecules;
(iii) defining three-dimensional coordinates for each of the pharmacophoric features; and
(iv) extracting the geometric arrangement from a triplet of the three-dimensional coordinates, wherein the triplet defines a triangle type and the triangle type is determined from an order of the pharmacophoric features;
(b) converting molecules into feature vectors by identifying subspaces within the joint pharmacophore space, each subspace having an associated subset of the pharmacophores with similar geometric arrangements, and the identifying step comprising the steps of:
(i) grouping the geometric arrangements according to the triangle type, wherein the geometric arrangements with similar triangle types are grouped as a triangle group; and
(ii) clustering the geometric arrangements in each triangle group into the subspaces according to distances between the geometric arrangements;
(c) assigning a biological activity property and a representative geometric arrangement for each subspace identified to correlate with a targeted biological activity; and
(d) storing the joint pharmacophore space, subspaces, biological activity properties, and representative geometric arrangements in the database of pharmacophores.

16. The computer-implemented apparatus of claim 15, wherein each triplet defines a triangle having vertices corresponding to the three-dimensional coordinates.

17. The computer-implemented apparatus of claim 15, wherein the order is user-defined.

18. The computer-implemented apparatus of claim 15, wherein the geometric arrangements in each triangle group that satisfy a user-defined similarity criteria are clustered as a subspace.

19. The computer-implemented apparatus of claim 15, wherein the step (ii) of clustering the geometric arrangements in each triangle group comprises the steps of:
computing one or more center geometric arrangements in the triangle group;

assigning the geometric arrangements in the triangle group to a closest one of the center geometric arrangements, thereby forming clusters of the geometric arrangements.

20. The computer-implemented apparatus of claim 19, wherein the center geometric arrangements in the triangle group are computed from the geometric arrangement having a minimum average distance to other geometric arrangements in the clusters of geometric arrangements.

21. The computer-implemented apparatus of claim 15, wherein step (c) of assigning a biological activity property comprises the steps of:
   (i) mining significant subspaces from among the identified subspaces, wherein the significant subspaces have a ratio of a number of geometric arrangements of active molecules to a total number of geometric arrangements that differs from an expected ratio;
   (ii) assigning a positive or negative biological activity property to each significant subspace;
   (iii) identifying a representative geometric arrangement for each significant subspace, wherein the representative geometric arrangement is most similar to other geometric arrangements in each significant subspace.

22. The computer-implemented apparatus of claim 21, wherein the subspaces are identified as significant subspaces if the ratio of the number of geometric arrangements of active molecules to the total number of geometric arrangements differs from the expected ratio in an amount greater than or equal to a user-defined threshold.

23. The computer-implemented apparatus of claim 22, wherein a positive biological activity property is assigned to a significant subspace having a ratio of the number of geometric arrangements of active molecules to the total number of geometric arrangements that is greater than the expected ratio and a negative biological activity property is assigned to a significant subspace having a ratio of the number of geometric arrangements of active molecules to the total number of geometric arrangements that is less than the expected ratio.

24. The computer-implemented apparatus of claim 15, wherein:
   the dataset is a dataset of known drugs;
   the step (c) of assigning the biological activity property and a representative geometric arrangement for each subspace identified to correlate with a targeted biological activity comprises the steps of:
      mining significant drug subspaces from among the identified subspaces, wherein the significant drug subspaces have a number of geometric arrangements associated with a drug corresponding to a single disease greater than an expected number of geometric arrangements; and
      tagging each of the mined significant drug subspaces with the corresponding disease.

25. The computer-implemented apparatus of claim 24, further comprising the steps of:
   generating an activity profile for each disease associated with the drug; and
   identifying a repurposed drug from the activity profile for more than one disease.

26. The computer-implemented apparatus of claim 15, wherein the triangle includes vertices corresponding to the three-dimensional coordinates of the triplet and the triangle type.

27. The computer-implemented apparatus of claim 26, wherein the triangle type is established by a user-defined order of the pharmacophoric features of the three-dimensional coordinates in the triplet.

28. A computer-implemented apparatus for classifying a query molecule with a database of pharmacophores, comprising:
   one or more computers; and
   one or more processes performed by the one or more computers, the processes configured to perform the steps of:
      (a) obtaining a database of the pharmacophores as generated in claim 15;
      (b) identifying at least one pharmacophoric feature for a query molecule;
      (c) defining a three-dimensional coordinate for each pharmacophoric feature of the query molecule;
      (d) extracting a plurality of geometric arrangements for the query molecule;
      (e) comparing the plurality of geometric arrangements of the query molecule to the representative geometric arrangements in the database of pharmacophores to classify the query molecule according to its similarity with the representative geometric arrangements; and
      (f) presenting the classification of the query molecule according to its similarity with the representative geometric arrangements.

* * * * *